United States Patent [19]
Reiter

[11] Patent Number: 6,087,392
[45] Date of Patent: Jul. 11, 2000

[54] (4-ARYLSULFONYLAMINO)-TETRAHYDROPYRAN-4-CARBOXYLIC ACID HYDROXAMIDES

[75] Inventor: Lawrence Alan Reiter, Mystic, Conn.

[73] Assignee: Pfizer Inc., New York, N.Y.

[21] Appl. No.: 09/380,436

[22] PCT Filed: Mar. 24, 1999

[86] PCT No.: PCT/IB99/00505

§ 371 Date: Sep. 1, 1999

§ 102(e) Date: Sep. 1, 1999

[87] PCT Pub. No.: WO99/52889

PCT Pub. Date: Oct. 21, 1999

Related U.S. Application Data

[60] Provisional application No. 60/081,364, Apr. 10, 1998.
[51] Int. Cl.⁷ .......................... A61K 31/44; A61K 31/35; C07D 309/14; C07D 405/12
[52] U.S. Cl. .................. 514/459; 514/336; 546/282.1; 549/424
[58] Field of Search ................ 549/424; 546/282.1; 514/336, 459

[56] References Cited

FOREIGN PATENT DOCUMENTS 606046   7/1994   European Pat. Off. .

*Primary Examiner*—Bernard Dentz
*Attorney, Agent, or Firm*—Peter C. Richardson; Paul H. Ginsburg; Garth Butterfield

[57] ABSTRACT

A compound of the formula

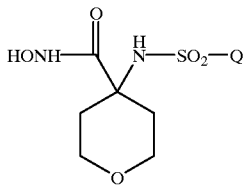

wherein Q is as defined above, are useful in the treatment of a condition selected from the group consisting of arthritis (including osteoarthritis and rheumatoid arthritis), inflammatory bowel disease, Crohn's disease, emphysema, chronic obstructive pulmonary disease, Alzheimer's disease, organ transplant toxicity, cachexia, allergic reactions, allergic contact hypersensitivity, cancer, tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neuro-degenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis and septic shock. In addition, the compounds of the present invention may be used in combination therapy with standard non-steroidal anti-inflammatory drugs (NSAID'S) and analgesics, and in combination with cytotoxic drugs such as adriamycin, daunomycin, cis-platinum, etoposide, taxol, taxotere and other alkaloids, such as vincristine, in the treatment of cancer.

11 Claims, No Drawings

(4-ARYLSULFONYLAMINO)-TETRAHYDROPYRAN-4-CARBOXYLIC ACID HYDROXAMIDES

This application claims priority under 35 U.S.C. 371 from PCT/IB95/00505 filed Mar. 24, 1999, which application claims priority from Verified Provisional Application 60/081364 filed Apr. 10, 1998.

BACKGROUND OF THE INVENTION

The present invention relates to (4-arylsulfonylamino)-tetrahydropyran-4-carboxylic acid hydroxamide derivatives, and to pharmaceutical compositions and methods of treatment.

The compounds of the present invention are inhibitors of zinc metalloendopeptidases, especially those belonging to the matrix metalloproteinase (also called MMP or matrixin) and reprolysin (also known as adamylsin) subfamilies of the metzincins (Rawlings, et al., *Methods in Enzymology*, 248, 183–228 (1995) and Stocker, et al., *Protein Science*, 4, 823–840 (1995)).

The MMP subfamily of enzymes, currently contains seventeen members (MMP-1, MMP-2, MMP-3, MMP-7, MMP-8, MMP-9, MMP-10, MMP-11, MMP-12, MMP-13, MMP-14, MMP-15, MMP-16, MMP-17, MMP-18, MMP-19, MMP-20). The MMP's are most well known for their role in regulating the turn-over of extracellular matrix proteins and as such play important roles in normal physiological processes such as reproduction, development and differentiation. In addition, the MMP's are expressed in many pathological situations in which abnormal connective tissue turnover is occurring. For example, MMP-13 an enzyme with potent activity at degrading type II collagen (the principal collagen in cartilage), has been demonstrated to be overexpressed in osteoarthritic cartilage (Mitchell, et al., *J. Clin. Invest.*, 97, 761 (1996)). Other MMPs (MMP-2, MMP-3, MMP-8, MMP-9, MMP-12) are also overexpressed in osteoarthritic cartilage and inhibition of some or all of these MMP's is expected to slow or block the accelerated loss of cartilage typical of joint diseases such as osteoarthritis or rheumatoid arthritis.

The mammalian reprolysins are known as ADAMs (A Disintegrin And Metalloproteinase) (Wolfberg, et al., *J. Cell Biol.*, 131, 275–278 (1995)) and contain a disintegrin domain in addition to a metalloproteinase-like domain. To date twenty three distinct ADAM's have been identified.

ADAM-17, also known as tumor necrosis factor-alpha converting enzyme (TACE), is the most well known ADAM. ADAM-17 (TACE) is responsible for cleavage of cell bound tumor necrosis factor-alpha (TNF-α, also known as cachectin). TNF-α is recognized to be involved in many infectious and auto-immune diseases (W. Friers, *FEBS Letters*, 285, 199 (1991)). Furthermore, it has been shown that TNF-α is the prime mediator of the inflammatory response seen in sepsis and septic shock (Spooner, et al., *Clinical Immunology and Immunopathology*, 62 S11 (1992)). There are two forms of TNF-α, a type II membrane protein of relative molecular mass 26,000 (26 kD) and a soluble 17 kD form generated from the cell bound protein by specific proteolytic cleavage. The soluble 17 kD form of TNF-α is released by the cell and is associated with the deleterious effects of TNF-α. This form of TNF-α is also capable of acting at sites distant from the site of synthesis. Thus, inhibitors of TACE prevent the formation of soluble TNF-α and prevent the deleterious effects of the soluble factor.

Select compounds of the invention are potent inhibitors of aggrecanase, an enzyme important in the degradation of cartilage aggrecan. Aggrecanase is also believed to be an ADAM. The loss of aggrecan from the cartilage matrix is an important factor in the progression of joint diseases such as osteoarthritis and rheumatoid arthritis and inhibition of aggrecanase is expected to slow or block the loss of cartilage in these diseases.

Other ADAMs that have shown expression in pathological situations include ADAM TS-1 (Kuno, et al., *J. Biol. Chem.*, 272, 556–562 (1997)), and ADAM's 10, 12 and 15 (Wu, et al., *Biochem. Biophys. Res. Comm.*, 235, 437–442, (1997)). As knowledge of the expression, physiological substrates and disease association of the ADAM's increases the full significance of the role of inhibition of this class of enzymes will be appreciated.

Diseases in which inhibition of MMP's and or ADAM's will provide therapeutic benefit include: arthritis (including osteoarthritis and rheumatoid arthritis), inflammatory bowel disease, Crohn's disease, emphysema, acute respiratory distress syndrome, asthma chronic obstructive pulmonary disease, Alzheimer's disease, organ transplant toxicity, cachexia, allergic reactions, allergic contact hypersensitivity, cancer, tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neurodegenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis, septic shock and other diseases characterized by metalloproteinase or ADAM expression.

This invention also relates to a method of using the compounds of the invention in the treatment of the above diseases in mammals, especially humans, and to the pharmaceutical compositions useful therefore.

It is recognized that different combinations of MMP's and ADAM's are expressed in different pathological situations. As such inhibitors with specific selectivities for individual ADAM's and/or MMP's may be preferred for individual diseases. For example, rheumatoid arthritis is an inflammatory joint disease characterized by excessive TNF levels and the loss of joint matrix constituents. In this case, a compound that inhibits TACE and aggrecanase as well as MMP's such as MMP-13 may be the preferred therapy. In contrast, in a less inflammatory joint disease such as osteoarthritis, compounds that inhibit matrix degrading MMP's such as MMP-13 but not TACE may be preferred.

The present inventors have also discovered that it is possible to design inhibitors with differential metalloprotease activity. Specifically, for example, the inventors have been able to design molecules which selectively inhibit matrix metalloprotease-13 (MMP-13) preferentially over MMP-1.

Matrix metalloproteinase and reprolysin inhibitors are well known in the literature. Specifically, PCT Publication WO 96/33172, published Oct. 24, 1996, refers to cyclic arylsulfonylamino hydroxamic acids that are useful as MMP inhibitors. U.S. Pat. No. 5,672,615, PCT Publication WO 97/20824, PCT Publication WO 98/08825, PCT publication WO 98/27069, and PCT Publication WO 98/34918, published Aug. 13, 1998, entitled "Arylsulfonyl Hydroxamic Acid Derivatives" all refer to cyclic hydroxamic acids that are useful as MMP inhibitors. PCT Publications WO 96/27583 and WO 98/07697, published Mar. 7, 1996 and Feb. 26, 1998, respectively, refer to arylsulfonyl hydroxamic acids. PCT Publication WO 98/03516, published Jan. 29, 1998 refers to phosphinates with MMP activity. PCT Publication 98/34915, published Aug. 13, 1998, entitled "N-Hydroxy-b-Sulfonyl Propionamide Derivatives," refers to propionythydroxamides as useful MMP inhibitors. PCT Publication WO 98/33768, published Aug. 6, 1998, entitled "Arylsulfonylamino Hydroxamic Acid Derivatives," refers to N-unsubstituted arylsulfonylamino hydroxamic acids. PCT Publication WO 98/30566, published Jul. 16, 1998, entitled "Cyclic Sulfone Derivatives," refers to cyclic sulfone hydroxamic acids as MMP inhibitors. U.S. Provisional Patent Application 60/55,208, filed Aug. 8, 1997, refers to biaryl hydroxamic acids as MMP inhibitors. U.S. Provisional Patent Application Ser. No. 60/55,207, filed Aug. 8, 1997, entitled "Aryloxyarylsulfonylamino Hydroxamic Acid Derivatives," refers to aryloxyarylsulfonyl hydroxamic acids as MMP inhibitors. U.S. Provisional Patent Application 60/62,766, filed October 24, 1997, entitled "The Use of MMP-13 Selective Inhibitors For The Treatment of Osteoarthritis and Other MMP Mediated Disorders," refers to the use of MMP-13 selective inhibitors to treat inflammation and other disorders. U.S. Provisional Patent Application Ser. No. 60/68,261, filed Dec. 19, 1997, refers to the use of MMP inhibitors to treat angiogenesis and other disorders. Each of the above referenced publications and applications is hereby incorporated by reference in its entirety.

SUMMARY OF THE INVENTION

The present invention relates to a compound of the formula

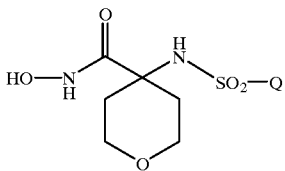

I or the pharmaceutically acceptable salt thereof, wherein Q is $(C_1-C_6)$alkyl, $(C_6-C_{10})$aryl, $(C_2-C_9)$heteroaryl, $(C_6-C_{10})$aryloxy$(C_1-C_6)$alkyl, $(C_6-C_{10})$aryloxy$(C_6-C_{10})$aryl, $(C_6-C_{10})$aryloxy$(C_2-C_9)$heteroaryl, $(C_6-C_{10})$aryl$(C_1-C_6)$alkyl, $(C_6-C_{10})$aryl$(C_6-C_{10})$aryl, $(C_6-C_{10})$aryl$(C_2-C_9)$heteroaryl, $(C_6-C_{10})$aryl$(C_6-C_{10})$aryl$(C_1-C_6)$alkyl, $(C_6-C_{10})$aryl$(C_6-C_{10})$aryl$(C_6-C_{10})$aryl, $(C_6-C_{10})$aryl$(C_6-C_{10})$aryl$(C_2-C_9)$heteroaryl, $(C_2-C_9)$heteroaryl$(C_1-C_6)$alkyl, $(C_2-C_9)$heteroaryl$(C_6-C_{10})$aryl, $(C_2-C_9)$heteroaryl$(C_2-C_9)$heteroaryl, $(C_6-C_{10})$aryl$(C_1-C_6)$alkoxy$(C_1-C_6)$alkyl, $(C_6-C_{10})$aryl$(C_1-C_6)$alkoxy$(C_6-C_{10})$aryl, $(C_6-C_{10})$aryl$(C_1-C_6)$alkoxy$(C_2-C_9)$heteroaryl, $(C_2-C_9)$heteroaryloxy$(C_1-C_6)$alkyl, $(C_2-C_9)$heteroaryloxy$(C_6-C_{10})$aryl, $(C_2-C_9)$heteroaryloxy$(C_2-C_9)$heteroaryl, $(C_2-C_9)$heteroaryl$(C_1-C_6)$alkoxy$(C_1-C_6)$alkyl, $(C_2-C_9)$heteroaryl$(C_1-C_6)$alkoxy$(C_6-C_{10})$aryl or $(C_2-C_9)$heteroaryl$(C_1-C_6)$alkoxy$(C_2-C_9)$heteroaryl;

wherein each $(C_6-C_{10})$aryl or $(C_2-C_9)$heteroaryl moieties of said $(C_6-C_{10})$aryl, $(C_2-C_9)$heteroaryl, $(C_6-C_{10})$aryloxy $(C_1-C_6)$alkyl, $(C_6-C_{10})$aryloxy$(C_6-C_{10})$aryl, $(C_6-C_{10})$aryloxy$(C_2-C_9)$heteroaryl, $(C_6-C_{10})$aryl$(C_1-C_6)$alkyl, $(C_6-C_{10})$aryl$(C_6-C_{10})$aryl, $(C_6-C_{10})$aryl$(C_2-C_9)$heteroaryl, $(C_6-C_{10})$aryl$(C_6-C_{10})$aryl$(C_1-C_6)$alkyl, $(C_6-C_{10})$aryl $(C_6-C_{10})$aryl$(C_6-C_{10})$aryl, $(C_6-C_{10})$aryl$(C_6-C_{10})$aryl $(C_2-C_9)$heteroaryl, $(C_2-C_9)$heteroaryl$(C_1-C_6)$alkyl, $(C_2-C_9)$heteroaryl$(C_6-C_{10})$aryl, $(C_2-C_9)$heteroaryl$(C_2-C_9)$heteroaryl, $(C_6-C_{10})$aryl$(C_1-C_6)$alkoxy$(C_1-C_6)$alkyl, $(C_6-C_{10})$aryl$(C_1-C_6)$alkoxy$(C_6-C_{10})$aryl, $(C_6-C_{10})$aryl $(C_1-C_6)$alkoxy$(C_2-C_9)$heteroaryl, $(C_2-C_9)$heteroaryloxy $(C_1-C_6)$alkyl, $(C_2-C_9)$heteroaryloxy$(C_6-C_{10})$aryl, $(C_2-C_9)$heteroaryloxy$(C_2-C_9)$heteroaryl, $(C_2-C_9)$heteroaryl$(C_1-C_6)$ alkoxy$(C_1-C_6)$alkyl, $(C_2-C_9)$heteroaryl$(C_1-C_6)$alkoxy $(C_6-C_{10})$aryl or $(C_2-C_9)$heteroaryl$(C_1-C_6)$alkoxy$(C_2-C_9)$ heteroaryl is optionally substituted on any of the ring carbon atoms capable of forming an additional bond by one or more substituents per ring independently selected from fluoro, chloro, bromo, $(C_1-C_6)$alkyl, $(C_1-C_6)$alkoxy, perfluoro $(C_1-C_3)$alkyl, perfluoro$(C_1-C_3)$alkoxy and $(C_6-C_{10})$ aryloxy;

or a pharmaceutically acceptable salt thereof.

The term "alkyl", as used herein, unless otherwise indicated, includes saturated monovalent hydrocarbon radicals having straight branched or cyclic moieties or combinations thereof.

The term "alkoxy", as used herein, includes O-alkyl groups wherein "alkyl" is defined above.

The term "aryl", as used herein, unless otherwise indicated, includes an organic radical derived from an aromatic hydrocarbon by removal of one hydrogen, such as phenyl or naphthyl, optionally substituted by 1 to 3 substituents selected from the group consisting of fluoro, chloro, bromo, perfluoro$(C_1-C_6)$alkyl (including trifluoromethyl), $(C_1-C_6)$alkoxy, $(C_6-C_{10})$aryloxy, perfluoro$(C_1-C_3)$alkoxy (including trifluoromethoxy and difluoromethoxy) and $(C_1-C_6)$alkyl.

The term "heteroaryl", as used herein, unless otherwise indicated, includes an organic radical derived from an aromatic heterocyclic compound by removal of one hydrogen, such as pyridyl, furyl, pyrroyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl, optionally substituted by 1 to 2 substituents selected from the group consisting of fluoro, chloro, trifluoromethyl, $(C_1-C_6)$alkoxy, $(C_6-C_{10})$aryloxy, trifluoromethoxy, difluoromethoxy and $(C_1-C_6)$alkyl. Preferred heteroaryls include pyridyl, furyl, thienyl, isothiazolyl, pyrazinyl, pyrimidyl, pyrazolyl, isoxazolyl, thiazolyl or oxazolyl. Most preferred include pyridyl, furyl or thienyl.

Preferred compounds of formula I include those wherein Q is optionally substituted $(C_6-C_{10})$aryl, $(C_6-C_{10})$aryl $(C_6-C_{10})$aryl, $(C_6-C_{10})$aryloxy$(C_6-C_{10})$aryl, $(C_6-C_{10})$ aryloxy$(C_2-C_9)$heteroaryl, $(C_2-C_9)$heteroaryl, $(C_2-C_9)$ heteroaryl$(C_2-C_9)$heteroaryl, $(C_6-C_{10})$aryl$(C_2-C_9)$ heteroaryl, $(C_2-C_9)$heteroaryl$(C_6-C_{10})$aryl, $(C_2-C_9)$ heteroaryloxy$(C_6-C_{10})$aryl, $(C_6-C_{10})$aryl$(C_1-C_6)$alkoxy $(C_6-C_{10})$aryl, or $(C_2-C_9)$heteroaryl$(C_1-C_6)$alkoxy$(C_6-C_{10})$ aryl.

Other preferred compounds of formula I include those wherein Q is optionally substituted $(C_6-C_{10})$aryloxy$(C_6C_{10})$ aryl.

Specific preferred compounds of formula I include the following:

4-[4-(4-Fluorophenoxy)benzenesulfonylamino] tetrahydropyran-4-carboxylic acid hydroxyamide;

4-[4-(4-Chlorophenoxy)benzenesulfonylamino] tetrahydropyran-4-carboxylic acid hydroxyamide;

4-[4-(Phenoxy)benzenesulfonylamino]tetrahydropyran-4-carboxylic acid hydroxyamide;

4-[4-(4-Pyridyloxy)benzenesulfonylamino] tetrahydropyran-4-carboxylic acid hydroxyamide;

4-[4-(4-Fluorophenyl)benzenesulfonylamino] tetrahydropyran-4-carboxylic acid hydroxyamide;

4-[4-(4-Fluorophenylmethoxy)bezenesulfonylamino] tetrahydropyran-4-carboxylic acid hydroxyamide;

4-[4-(Phenylmethoxy)benzenesulfonylamino] tetrahydropyran-4-carboxylic acid hydroxyamide; and 4-[4-(4-Fluorophenylethoxy)benzenesulfonylamino] tetrahydropyran-4-carboxylic acid hydroxyamide.

The present invention also relates to a pharmaceutical composition for the treatment of a condition selected from the group consisting of arthritis (including osteoarthritis and rheumatoid arthritis), inflammatory bowel disease, Crohn's disease, emphysema, chronic obstructive pulmonary disease, Alzheimer's disease, organ transplant toxicity, cachexia, allergic reactions, allergic contact hypersensitivity, cancer (such as solid tumor cancer including colon cancer breast cancer, lung cancer and prostrate cancer and hematopoietic malignancies including leukemias and lymphomas), tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neuro-degenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis, septic shock and other diseases characterized by metalloproteinase activity and other diseases characterized by mammalian reprolysin activity in a mammal, including a human, comprising an amount of a compound of formula I or a pharmaceutically acceptable salt thereof effective in such treatments and a pharmaceutically acceptable carrier.

The present invention also relates to a pharmaceutical composition for the inhibition of (a) matrix metalloproteinases or other metalloproteinases involved in matrix degradation, or (b) a mammalian reprolysin (such as aggrecanase or ADAM's TS-1, 10, 12, 15 and 17, most preferably ADAM-17) in a mammal, including a human, comprising an effective amount of a compound of formula I or a pharmaceutically acceptable salt thereof.

The present invention also relates to a method for treating a condition selected from the group consisting of arthritis (including osteoarthritis and rheumatoid arthritis), inflammatory bowel disease, Crohn's disease, emphysema, chronic obstructive pulmonary disease, Alzheimer's disease, organ transplant toxicity, cachexia, allergic reactions, allergic contact hypersensitivity, cancer, tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neuro-degenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis, septic shock and other diseases characterized by metalloproteinase activity and other diseases characterized by mammalian reprolysin activity in a mammal, including a human, comprising administering to said mammal an amount of a compound of formula I or a pharmaceutically acceptable salt thereof effective in treating such a condition.

The present invention also relates to a method for the inhibition of (a) matrix metalloproteinases or other metalloproteinases involved in matrix degradation, or (b) a mammalian reprolysin (such as aggrecanase or ADAM's TS-1, 10, 12, 15 and 17, preferably ADAM-17) in a mammal, including a human, comprising administering to said mammal an effective amount of a compound of formula I or a pharmaceutically acceptable salt thereof.

This invention also encompasses pharmaceutical compositions containing prodrugs of compounds of the formula I. This invention also encompasses methods of treating or preventing disorders that can be treated or prevented by the inhibition of matrix metalloproteinases or the inhibition of mammalian reprolysin comprising administering prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain.

One of ordinary skill in the art will appreciate that the compounds of the invention are useful in treating a diverse array of diseases. One of ordinary skill in the art will also appreciate that when using the compounds of the invention in the treatment of a specific disease that the compounds of the invention may be combined with various existing therapeutic agents used for that disease.

For the treatment of rheumatoid arthritis, the compounds of the invention may be combined with agents such as TNF-α inhibitors such as anti-TNF monoclonial antibodies and TNF receptor immunoglobulin molecules (such as Enbrel®), low dose methotrexate, lefunimide, hydroxychloroquine, d-penicilamine, auranofin or parenteral or oral gold.

The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib and rofecoxib, analgesics and intraarticular therapies such as corticosteroids and hyaluronic acids such as hyalgan and synvisc.

The compounds of the present invention may also be used in combination with anticancer agents such as endostatin and angiostatin or cytotoxic drugs such as adriamycin, daunomycin, cis-platinum, etoposide, taxol, taxotere and alkaloids, such as vincristine, and antimetabolites such as methotrexate.

The compounds of the present invention may also be used in combination with cardiovascular agents such as calcium channel blockers, lipid lowering agents such as statins, fibrates, beta-blockers, Ace inhibitors, Angiotensin-2 receptor antagonists and platelet aggregation inhibitors.

The compounds of the present invention may also be used in combination with CNS agents such as antidepressants (such as sertraline), anti-Parkinsonian drugs (such as deprenyl, L-dopa, requip, miratex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as Aricept, tacrine, COX-2 inhibitors, propentofylline or metryfonate.

The compounds of the present invention may also be used in combination with osteoporosis agents such as droloxifene or fosomax and immunosuppressant agents such as FK-506 and rapamycin.

DETAILED DESCRIPTION OF THE INVENTION

The following reaction Scheme illustrates the preparation of the compounds of the present invention. Unless otherwise indicated, Q in the reaction Schemes and the discussion that follows is defined as above.

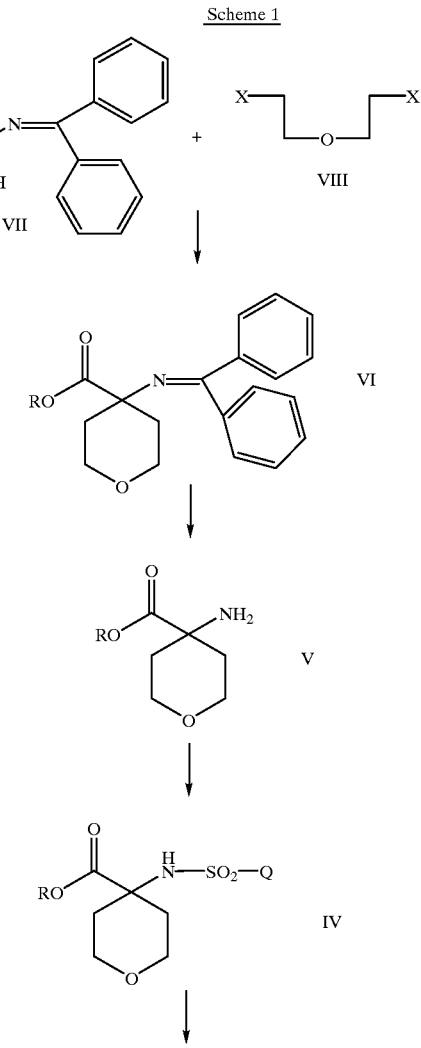

-continued

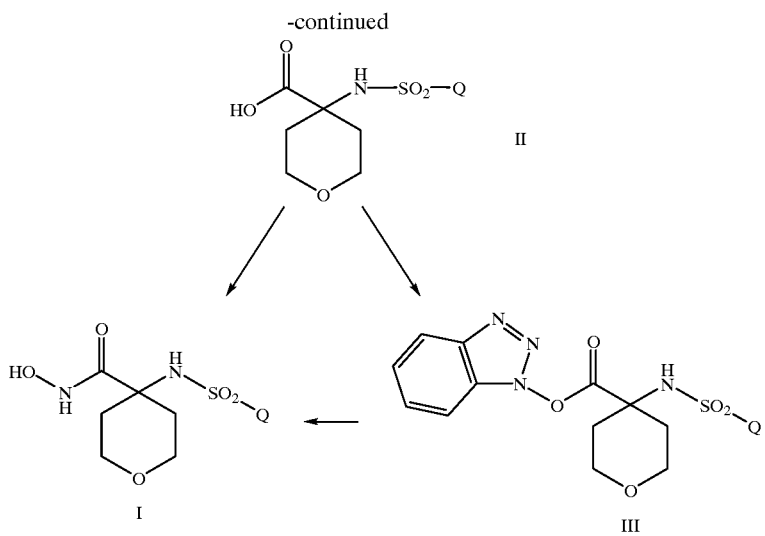

Scheme 1 refers to the preparation of compounds of the formula I.

Referring to Scheme 1, the compound of formula I is prepared from the carboxylic acid of formula II by treatment with 1-(3-dimethylaminopropyl)-3-ethylcarbodiimide and 1-hydroxybenztriazole in a polar solvent, such as N,N-dimethylformamide, followed by the addition of hydroxylamine to the reaction mixture after a time period between about 15 minutes to about 1 hour, preferably about 30 minutes. The hydroxylamine is preferably generated in situ from a salt form, such as hydroxylamine hydrochloride, in the presence of a base, such as triethylamine.

Alternatively the compound of formula I can be prepared from a compound of formula II by reaction with a protected derivative of hydroxylamine or its salt form, where the hydroxyl group is protected as a tert-butyl, benzyl, allyl or 2-trimethylsilylethyl ether. Removal of the hydroxyl protecting group is carried out by hydrogenolysis for a benzyl protecting group (5% palladium on barium sulfate is the preferred catalyst) or treatment with a strong acid, such as trifluoroacetic acid, for a tert-butyl protecting group. The allyl protecting group may be removed by treatment with tributylinhydride and acetic acid in the presence of catalytic bis(triphenylphosphine) palladium(II)chloride. The 2-trimethylsilylethyl ether may be removed by reaction with a strong acid such as trifluoroacetic acid or by reaction with a fluoride source such as boron trifluoride etherate.

The reaction of II with hydroxylamine, a salt of hydroxylamine, a protected derivative of hydroxylamine or a salt of a protected derivative of hydroxylamine may also be carried out in the presence of (benztriazol-1-yloxy)tris(dimethylamino)phosphonium hexafluorophosphate and a base such as triethylamine in an inert solvent, such as methylene chloride. The reaction mixture is stirred at a temperature between about 0° C. to about 50° C., preferably room temperature, for a time period between about 1 hour to about 3 days, preferably about 1 day.

Another procedure for converting a compound of formula II to a compound of formula I is to react the compound of formula II with O-benzylhydroxylamine hydrochloride in the presence of (benztriazol-1-yloxy)tris(dimethylamino) phosphonium hexafluorophosphate and triethylamine using methylene chloride as solvent. Subsequent removal of the O-benzyl protecting group to afford a compound of formula I is then carried out by hydrogenolysis under 3 atmospheres hydrogen at room temperature using 5% palladium on barium sulfate as catalyst. The preferred solvent is methanol. The reaction time may vary from about 1 hour to about 2 days (8 hours is preferred).

The preferred procedure for converting a compound of formula II to a compound of formula I is to react the compound of formula II with oxalyl chloride in methylene chloride in the presence of a catalytic amount of DMF for 16 hours. The resulting add chloride is reacted at 0° C. with N, O- bis trimethylsilyl hydroxylamine formed by reacting hydroxyamine hydrochloride with chlorotrimethyl-silane in pyridine at 0° C. to room temperature. The product of formula I is obtained after a few hours reactions at 0° C. to room temperature followed by an acidic aqueous workup which removes all trimethyl silyl residues.

In certain instances it is preferred to obtain the compound of formula I by reaction of hydroxylamine, a salt of hydroxylamine, a protected derivative of hydroxylamine or a salt of a protected derivative of hydroxylamine with an activated ester of formula III. The reaction is carried out in an inert solvent, such as N,N-dimethyl-formamide at a temperature ranging from about room temperature to about 80° C., preferably about 60° C. for a time period of about 1 hour to about 2 days. If a protected derivative of hydroxylamine or a salt of a protected derivative of hydroxylamine is used, removal of the protecting group is carried out as described above. The activated ester derivative of formula III is obtained by treatment of the compound of formula II with (benztriazol-1-yloxy)tris(dimethylamino)-phosphonium hexafluorophosphate and a base such as triethylamine in an inert solvent, such as methylene chloride. The reaction mixture is stirred at a temperature between about 0° C. to about 50° C., preferably room temperature, for a time period between about 1 hour to about 3 days, preferably about 1 day.

The intermediate compound of formula II is prepared by saponification of a compound of formula IV. The reaction is carried out at in a solvent, such as aqueous ethanol, with an excess of a metal hydroxides, such as sodium hydroxide or lithium hydroxide, at a temperature of about 20° C. to about 100° C., (i.e. room temperature to the reflux temperature of the solvent), preferably about 80° C. The reaction mixture is normally agitated at room temperature for a time period between about 30 minutes to about 1 week, preferably about 16 hours.

The compound of formula IV is prepared by reacting a compound of formula V with a reactive functional derivative of a sulfonic acid ($QSO_2OH$), such as the sulfonyl chloride ($QSO_2Cl$), in the presence of a base. Suitable bases include sodium hydroxide, triethylamine or diisopropylethylamine, preferably triethylamine. Suitable solvents include dimethylformamide (DMF), methylene chloride, tetrahydrofuran, dioxane, water or acetonitrile, preferably DMF. The reaction mixture is stirred at a temperature between about 0° C. to about 50° C., preferably at about 20° C. to about 25° C. (i.e. room temperature), for a time period between about 10 minutes to about 2 days, preferably about 1 day.

The compound of formula V is prepared by hydrolysis of a compound of formula IV. Specifically, the compound of formula VI is treated with aqueous acid, preferably in the presence of an immiscible organic solvent such ethyl ether, diisopropyl ether or methylene chloride. Suitable acids include hydrochloric and sulfuric. The reaction mixture is stirred at a temperature between about 0° C. to about 50° C., preferably at about 20° C. to about 25° C. (i.e. room temperature), for a time period between about 10 minutes to about 2 days: preferably about 1 day.

The compound of formula VI is prepared by reaction of the amino acid derivative of the formula VII with a compound of the formula VIII in the presence of a base and a solvent, wherein X is Cl, Br, I, tosylate or mesylate. Suitable bases include ethlyene glycol, sodium hydride, lithium diisopropylamide, or sodium hexamethyl disilazide. Suitable solvents include dimethylether, dimethylformamide, tetrahydrofuran or dimethylsulfoxide. The reaction mixture is stirred at a temperature between about −20° C. to about 25° C., preferably at about 0° C. to about 20° C. (i.e. room temperature), for a time period between about 10 minutes to about 2 days, preferably about 1 day.

The compounds of formulae VII and VIII can be prepared by methods well known to those of ordinary skill in the art Examples of such compounds include methylglycine benzophenone imine and ethyl glycine benzophenone imine.

Pharmaceutically acceptable salts of the acidic compounds of the invention are salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris-hydroxymethyl)-methylammonium slats.

Similarly acid addition salts, such as of mineral acids, organic carboxylic and organic sulfonic acids e.g. hydrochloric acid, methanesulfonic acid, maleic acid, are also possible provided a basic group, such as pyridyl, constitutes part of the structure.

The ability of the compounds of formula I or their pharmaceutically acceptable salts (hereinafter also referred to as the compounds of the present invention) to inhibit metalloproteinases or mammalian reprolysin and, consequently, demonstrate their effectiveness for treating diseases characterized by metalloproteinase or the production of tumor necrosis factor is shown by the following in vitro assay tests.

Biological Assay Inhibition of Human Collagenase (MMP-1)

Human recombinant collagenase is activated with trypsin. The amount of trypsin is optimized for each lot of collagenase-1 but a typical reaction uses the following ratio: 5 μg trypsin per 100 μg of collagenase. The trypsin and collagenase are incubated at room temperature for 10 minutes then a five fold excess (50 mg/10 mg trypsin) of soybean trypsin inhibitor is added.

Stock solutions (10 mM) of inhibitors are made up in dimethylsulfoxide and then diluted using the following scheme:

10 mM→120 μM→12 μM→1.2 μM→0.12 μM

Twenty-five microliters of each concentration is then added in triplicate to appropriate wells of a 96 well microfluor plate. The final concentration of inhibitor will be a 1:4 dilution after addition of enzyme and substrate. Positive controls (enzyme, no inhibitor) are set up in wells D7–D12 and negative controls (no enzyme, no inhibitors) are set in wells D1–D6.

Collagenase-1 is diluted to 240 ng/ml and 25 ml is then added to appropriate wells of the microfluor plate. Final concentration of collagenase in the assay is 60 ng/ml.

Substrate (DNP-Pro-Cha-Gly-Cys(Me)-His-Ala-Lys (NMA)-$NH_2$) is made as a 5 mM stock in dimethylsulfoxide and then diluted to 20 μM in assay buffer. The assay is initiated by the addition of 50 ml substrate per well of the microfluor plate to give a final concentration of 10 mM.

Fluorescence readings (360 nM excitaton, 460 nm emission) are taken at time 0 and then at 20 minute intervals. The assay is conducted at room temperature with a typical assay time of 3 hours Fluorescence versus time is then plotted for both the blank and collagenase containing samples (data from triplicate determinations is averaged). A time point that provides a good signal (at least five fold over the blank) and that is on a linear part of the curve (usually around 120 minutes) is chosen to determine $IC_{50}$ values. The zero time is used as a blank for each compound at each concentration and these values are subtracted from the 120 minute data. Data is plotted as inhibitor concentration versus % control (inhibitor fluorescence divided by fluorescence of collagenase alone× 100). $IC_{50}$'s are determined from the concentration of inhibitor that gives a signal that is 50% of the control.

If $IC_{50}$'s are reported to be less than 0.03 mM then the inhibitors are assayed at concentrations of 0.3 mM, 0.03 mM, and 0.003 mM.

Inhibition of Gelatinase (MMP-2)

Human recombinant 72 kD gelatinase (MMP-2, gelatinase A) is activated for 16–18 hours with 1 mM p-aminophenyl-mercuric acetate (from a freshly prepared 100 mM stock in 0.2 N NaOH) at 40° C., rocking gently.

10 mM dimethylsulfoxide stock solutions of inhibitors are diluted serially in assay buffer (50 mM TRIS, pH 7.5, 200 mM NaCl, 5 mM $CaCl_2$, 20 μM $ZnCl_2$ and 0.02% BRIJ-35 (vol./vol.)) using the following scheme:

10 mM→120 μM→12 μM→1.2 μM→0.12 μM

Further dilutions are made as necessary following this same scheme. A minimum of four inhibitor concentrations for each compound are performed in each assay. 25 μL of each concentration is then added to triplicate wells of a black 96 well U-bottomed microfluor plate. As the final assay volume is 100 μL, final concentrations of inhibitor are the result of a further 1:4 dilution (i.e. 30 μM→3 μM→0.3 μM→0.03 μM, etc.). A blank (no enzyme, no inhibitor) and a positive enzyme control (with enzyme, no inhibitor) are also prepared in triplicate.

Activated enzyme is diluted to 100 ng/mL in assay buffer, 25 μL per well is added to appropriate wells of the microplate. Final enzyme concentration in the assay is 25 ng/mL (0.34 nM).

A five mM dimethylsulfoxide stock solution of substrate (Mca-Pro-Leu-Gly-Leu-Dpa-Ala-Arg-NH$_2$) is diluted in assay buffer to 20 μM. The assay is initiated by addition of 50 μL of diluted substrate yielding a final assay concentration of 10 μM substrate. At time zero, fluorescence reading (320 excitation; 390 emission) is immediately taken and subsequent readings are taken every fifteen minutes at room temperature with a PerSeptive Biosystems CytoFluor Multi-Well Plate Reader with the gain at 90 units.

The average value of fluorescence of the enzyme and blank are plotted versus time. An early time point on the linear part of this curve is chosen for IC$_{50}$ determinations. The zero time point for each compound at each dilution is subtracted from the latter time point and the data then expressed as percent of enzyme control (inhibitor fluorescence divided by fluorescence of positive enzyme control× 100). Data is plotted as inhibitor concentration versus percent of enzyme control. IC$_{50}$'s are defined as the concentration of inhibitor that gives a signal that is 50% of the positive enzyme control.

Inhibition of Stromelysin Activity (MMP-3)

Human recombinant stromelysin (MMP-3, stromelysin-1) is activated for 20–22 hours with 2 mM p-aminophenyl-mercuric acetate (from a freshly prepared 100 mM stock in 0.2 N NaOH) at 37° C.

10 mM dimethylsulfoxide stock solutions of inhibitors are diluted serially in assay buffer (50 mM TRIS, pH 7.5, 150 mM NaCl, 10 mM CaCl$_2$ and 0.05% BRIJ-35 (vol.vol.)) using the following scheme:

10 mM→120 μM→12 μM→1.2 μM→0.12 μM

Further dilutions are made as necessary following this same scheme. A minimum of four inhibitor concentrations for each compound are performed in each assay. 25 μL of each concentration is then added to triplicate wells of a black 96 well U-bottomed microfluor plate. As the final assay volume is 100 μL, final concentrations of inhibitor are the result of a further 1:4 dilution (i.e. 30 μM→3 μM→0.3 μM→0.03 μM, etc.). A blank (no enzyme, no inhibitor) and a positive enzyme control (with enzyme, no inhibitor) are also prepared in triplicate.

Activated enzyme is diluted to 200 ng/mL in assay buffer, 25 μL per well is added to appropriate wells of the microplate. Final enzyme concentration in the assay is 50 ng/mL (0.875 nM).

A ten mM dimethylsulfoxide stock solution of substrate (Mca-Arg-Pro-Lys-Pro-Val-Glu-Nva-Trp-Arg-Lys(Dnp)-NH$_2$) is diluted in assay buffer to 6 μM. The assay is initiated by addition of 50 μL of diluted substrate yielding a final assay concentration of 3 μM substrate. At time zero, fluorescence reading (320 excitation; 390 emission) is immediately taken and subsequent readings are taken every fifteen minutes at room temperature with a PerSeptive Biosystems CytoFluor Multi-Well Plate Reader with the gain at 90 units.

The average value of fluorescence of the enzyme and blank are plotted versus time. An early time point on the linear part of this curve is chosen for IC$_{50}$ determinations. The zero time point for each compound at each dilution is subtracted from the latter time point and the data then expressed as percent of enzyme control (inhibitor fluorescence divided by fluorescence of positive enzyme control× 100). Data is plotted as inhibitor concentration versus percent of enzyme control. IC$_{50}$'s are defined as the concentration of inhibitor that gives a signal that is 50% of the positive enzyme control.

Inhibition of MMP-13

Human recombinant MMP-13 is activated with 2 mM APMA (p-aminophenyl mercuric acetate) for 2.0 hours, at 37° C. and is diluted to 240 ng/ml in assay buffer (50 mM Tris, pH 7.5, 200 mM sodium chloride, 5 mM calcium chloride, 20 mM zinc chloride, 0.02% brij 35). Twenty-five microliters of diluted enzyme is added per well of a 96 well microfluor plate. The enzyme is then diluted in a 1:4 ratio in the assay by the addition of inhibitor and substrate to give a final concentration in the assay of 60 ng/ml.

Stock solutions (10 mM) of inhibitors are made up in dimethylsulfoxide and then diluted in assay buffer as per the inhibitor dilution scheme for inhibition of human collagenase-1 (MMP-1): Twenty-five microliters of each concentration is added in triplicate to the microfluor plate. The final concentrations in the assay are 30 mM, 3 mmM, 0.3 m mM, and 0.03 mmM.

Substrate (Dnp-Pro-Cha-Gly-Cys(Me)-His-Ala-Lys (NMA)-NH$_2$) is prepared as for inhibition of human collagenase (MMP-1) and 50 μl is added to each well to give a final assay concentration of 10 μM. Fluorescence readings (360 nM excitation; 450 nM emission) are taken at time 0 and every 5 minutes for 1 hour.

Positive controls and negative controls are set up in triplicate as outlined in the MMP-1 assay.

IC$_{50}$'s are determined as per inhibition of human collagenase (MMP-1). If IC$_{50}$'s are reported to be less than 0.03 mM, inhibitors are then assayed at final concentrations of 0.3 mM, 0.03 mmM, 0.003 mmM and 0.0003 mM.

Inhibition of TNF Production

The ability of the compounds or the pharmaceutically acceptable salts thereof to inhibit the production of TNF and, consequently, demonstrate their effectiveness for treating diseases involving the production of TNF is shown by the following in vitro assay:

Human mononuclear cells were isolated from anti-coagulated human blood using a one-step Ficoll-hypaque separation technique. (2) The mononuclear cells were washed three times in Hanks balanced salt solution (HBSS) with divalent cations and resuspended to a density of 2×10$^6$/ml in HBSS containing 1% BSA. Differential counts determined using the Abbott Cell Dyn 3500 analyzer indicated that monocytes ranged from 17 to 24% of the total cells in these preparations.

180 μl of the cell suspension was aliquoted into flat bottom 96 well plates (Costar). Additions of compounds and LPS (100 ng/ml final concentration) gave a final volume of 200 μl. All conditions were performed in triplicate. After a four hour incubation at 37° C. in an humidified CO$_2$ incubator, plates were removed and centrifuged (10 minutes at approximately 250×g) and the supernatants removed and assayed for TNFa using the R&D ELISA Kit.

Inhibition of Soluble TNF-α Production

The ability of the compounds or the pharmaceutically acceptable salts thereof to inhibit the cellular release of TNF-α and, consequently, demonstrate their effectiveness for treating diseases involving the disregulation of soluble TNF-α is shown by the following in vitro assay:

Method for the Evaluation of Recombinant TNF-α Converting Enzyme Activity Expression of Recombinant TACE A DNA fragment coding for the signal sequence, preprodomain, prodomain and catalytic domain of TACE (amino acids 1–473), can be amplified by polymerase chain reaction using a human lung cDNA library as a template. The amplified fragment is then cloned into pFastBac vector. The DNA sequence of the insert is confirmed for both the strands. A bacmid prepared using pFastBac in *E. coli* DH10Bac is transfected into SF9 insect cells. The virus particles is then amplified to P1, P2, P3 stages. The P3 virus is infected into both Sf9 and High Five insect cells and grown at 27° C. for 48 hours. The medium is collected and used for assays and further purification.

Preparation of Fluorescent Quenched Substrate

A model peptidic TNF-α substrate (LY-LeucineAlanineGlutamineAlanineValineArginineSerine-SerineLysine(CTMR)-Arginine (LY=Lucifer Yellow; CTMR=Carboxytetramethyl-Rhodamine)) is prepared and the concentration estimated by absorbance at 560 nm ($E_{560}$, 60,000 M-1CM-1) according to the method of Geoghegan, KF, "Improved method for converting an unmodified peptide to an energy-transfer substrate for a proteinase." *Bioconjugate Chem.* 7, 385–391 (1995). This peptide encompasses the cleavage cite on pro-TNF which is cleaved in vivo by TACE.

Expression of Recombinant TACE

A DNA fragment coding for the signal sequence, preprodomain, prodomain and catalytic domain of TACE (amino acids 1–473), is amplified by polymerase chain reaction using a human lung cDNA library as a template. The amplified fragment is cloned into pFastBac vector. The DNA sequence of the insert is confirmed for both the strands. A bacmid prepared using pFastBac in *E. coli* DH10Bac is transfected into SF9 insect cells. The virus particles were amplified to P1, P2, P3 stages. The P3 virus is infected into both Sf9 and High Five insect cells and grown at 27° C. for 48 hours. The medium is collected and used for assays and further purification.

Enzyme Reaction

The reaction, carried out in a 96 well plate (Dynatech), is comprised of 70 μl of buffer solution (25 mM Hepes-HCl, pH7.5, plus 20 uM $ZnCl_2$), 10 μl of 100 μM fluorescent quenched substrate, 10 μl of a DMSO (5%) solution of test compound, and an amount of r-TACE enzyme which will cause 50% cleavage in 60 minutes—in a total volume of 100 μl. The specificity of the enzyme cleavage at the amide bond between alanine and valine is verified by HPLC and mass spectrometry. Initial rates of cleavage are monitored by measuring the rate of increase in fluorescence at 530 nm (excitation at 409 nm) over 30 minutes. The experiment is controlled as follows: 1) for background fluorescence of substrate; 2) for fluorescence of fully cleaved substrate; 3) for fluorescence quenching or augmentation from solutions containing test compound.

Data is analyzed as follows. The rates from the non-test compound containing "control" reactions were averaged to establish the 100% value. The rate of reaction in the presence of test compound was compared to that in the absence of compound, and tabulated as "percent of non-test compound containing control. The results are plotted as "% of control" vs. the log of compound concentration and a half-maximal point or $IC_{50}$ value determined.

All of the compounds of the invention have $IC_{50}$ of less than 1 μM, preferably less than 50 nM. Most preferred compounds of the invention are at least 100 fold less potent against r-MMP-1 than in the above TACE assay.

Human Monocyte Assay

Human mononuclear cells are isolated from anti-coagulated human blood using a one-step Ficoll-hypaque separation technique. (2) The mononuclear cells are washed three times in Hanks balanced salt solution (HBSS) with divalent cations and resuspended to a density of $2 \times 10^6$/ml in HBSS containing 1% BSA Differential counts determined using the Abbott Cell Dyn 3500 analyzer indicated that monocytes ranged from 17 to 24% of the total cells in these preparations.

180 m of the cell suspension was aliquoted into flat bottom 96 well plates (Costar). Additions of compounds and LPS (100 ng/ml final concentration) gave a final volume of 200 μl. All conditions were performed in triplicate. After a four hour incubation at 37° C. in an humidified $CO_2$ incubator, plates were removed and centrifuged (10 minutes at approximately 250×g) and the supernatants removed and assayed for TNF-α using the R&D ELISA Kit.

Aggrecanase Assay

Primary porcine chondrocytes from articular joint cartilage are isolated by sequential trypsin and collagenase digestion followed by collagenase digestion overnight and are plated at $2 \times 10^5$ cells per well into 48 well plates with 5 μCi/ml $^{35}$S(1000 Ci/mmol) sulphur in type I collagen coated plates. Cells are allowed to incorporate label into their proteoglycan matrix (approximately 1 week) at 37° C., under an atmosphere of 5% $CO_2$.

The night before initiating the assay, chondrocyte monolayers are washed two times in DMEM/1% PSF/G and then allowed to incubate in fresh DMEM/1% FBS overnight.

The following morning chondrocytes are washed once in DMEM/1%PSF/G. The final wash is allowed to sit on the plates in the incubator while making dilutions.

Media and dilutions can be made as described in the Table below.

| | |
|---|---|
| Control Media | DMEM alone (control media) |
| IL-1 Media | DMEM + IL-1 (5 ng/ml) |
| Drug Dilutions | Make all compounds stocks at 10 mM in DMSO. Make a 100 uM stock of each compound in DMEM in 96 well plate. Store in freezer overnight. The next day perform serial dilutions in DMEM with IL-1 to 5 uM, 500 nM, and 50 nM. Aspirate final wash from wells and add 50 ul of compound from above dilutions to 450 ul of IL-1 media in appropriate wells of the 48 well plates. Final compound concentrations equal 500 nM, 50 nM, and 5 nM. All samples completed in triplicate with Control and IL-1 alone samples on each plate. |

Plates are labeled and only the interior 24 wells of the plate are used. On one of the plates, several columns are designated as IL-1 (no drug) and Control (no IL-1, no drug). These control columns are periodically counted to monitor 35S-proteoglycan release. Control and IL-1 media are added to wells (450 ul) followed by compound (50 ul) so as to initiate the assay. Plates are incubated at 37° C., with a 5% $CO_2$ atmosphere.

At 40–50% release (when CPM from IL-1 media is 4–5 times control media) as assessed by liquid scintillation counting (LSC) of media samples, the assay is terminated (9–12 hours). Media is removed from all wells and placed in scintillation tubes. Scintillate is added and radioactive counts are acquired (LSC). To solubilize cell layers, 500 ul of papain digestion buffer (0.2 M Tris, pH 7.0, 5 mM EDTA, 5 mM DTT, and 1 mg/ml papain) is added to each well. Plates with digestion solution are incubated at 60° C. overnight The cell layer is removed from the plates the next day and placed in scintillation tubes. Scintillate is then added, and samples counted (LSC).

The percent of released counts from the total present in each well is determined. Averages of the triplicates are made with control background subtracted from each well. The percent of compound inhibition is based on IL-1 samples as 0% inhibition (100% of total counts).

For administration to mammals, including humans, for the inhibition of matrix metalloproteinases or the production of tumor necrosis factor (TNF), a variety of conventional routes may be used including orally, parenterally and topically. In general, the active compound will be administered orally or parenterally at dosages between about 0.1 and 25 mg/kg body weight of the subject to be treated per day, preferably from about 0.3 to 5 mg/kg. However, some variation in dosage will necessarily occur depending on the condition of the subject being treated. The person responsible for administration will, in any event, determine the appropriate dose for the individual subject.

The compounds of the present invention can be administered in a wide variety of different dosage forms, in general, the therapeutically effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelation and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof. In the case of animals, they are advantageously contained in an animal feed or drinking water in a concentration of 5–5000 ppm, preferably 25 to 500 ppm.

For parenteral administration (intramuscular, intraperitoneal, subcutaneous and intravenous use) a sterile injectable solution of the active ingredient is usually prepared. Solutions of a therapeutic compound of the present invention in either sesame or peanut oil or in aqueous propylene glycol may be employed. The aqueous solutions should be suitably adjusted and buffered, preferably at a pH of greater than 8, if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. In the case of animals, compounds can be administered intramuscularly or subcutaneously at dosage levels of about 0.1 to 50 mg/kg/day, advantageously 0.2 to 10 mg/kg/day given in a single dose or up to 3 divided doses.

For topical ocular administration, direct application to the affected eye may be employed in the form of a formulation as eyedrops, aerosol, gels or ointments, or can be incorporated into collagen (such as poly-2-hydroxyethylmethacrylate and co-polymers thereof), or a hydrophilic polymer shield. The materials can also be applied as a contact lens or via a local reservoir or as a subconjunctival formulation.

For intraorbital administration a sterile injectable solution of the active ingredient is usually prepared. Solutions of a therapeutic compound of the present invention in an aqueous solution or suspension (particle size less than 10 micron) may be employed. The aqueous solutions should be suitably adjusted and buffered, preferably at a pH between 5 and 8, if necessary and the liquid diluent first rendered isotonic. Small amounts of polymers can be added to increase viscosity or for sustained release (such as cellulosic polymers, Dextran, polyethylene glycol, or alginic acid). These solutions are suitable for intraorbital injection purposes. The preparation of all these solutions under sterile conditions is readily accomplished by standard pharmaceutical techniques well known to those skilled in the art In the case of animals, compounds can be administered intraorbitally at dosage levels of about 0.1 to 50 mg/kg/day, advantageously 0.2 to 10 mg/kg/day given in a single dose or up to 3 divided doses.

The active compounds of the invention may also be formulated in rectal compositions such as suppositories or retention enemas, eg., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

The present invention is illustrated by the following Preparations and Examples, but it is not limited to the details thereof.

EXAMPLE 1

4-[4-(4-Fluorophenoxy)Benzenesulfonylamino]-Tetrahydro Pyran-4-Carboxylic Acid Hydroxyamide (A) 4-[N-(Diphenylmethylene)Amino] Tetrahydropyran-4-Carboxylic Acid Ethyl Ester To a suspension of sodium hydride (6.56 grams. 0.164 mole) in ethylene glycol dimethyl ether (150 mL) at 0° C.

was added a solution of the N-(diphenylmethylene)glycine ethyl ester (20.60 grams, 0.07398 mole) in ethylene glycol dimethyl ether (50 mL) dropwise via addition funnel. A solution of 2-bromoethyl ether (23.21 grams, 0.090 mole) in ethylene glycol dimethyl ether (50 mL) was then added, in 10 mL portions over approximately 5 minutes, to the ethylene glycol dimethyl ether solution. The ice bath was removed and the reaction was stirred at room temperature for 16 hours. The mixture was diluted with diethyl ether and washed with water. The aqueous layer was extracted with diethyl ether. The combined organic extracts were washed with brine, dried over magnesium sulfate, and concentrated to afford a cloudy yellow oil (28.692 grams). Chromatography on silica gel eluting first with 4 L of 5% ethyl acetate/hexane followed by 4 liters of 10% ethyl acetate/hexane gave 4-[N-(diphenylmethylene)amino] tetrahydropyran-4-carboxylic acid ethyl ester as a clear yellow oil (16.114 g, 64%).

$^1$HNMR (CDCl$_3$) δ 7.58 (d, 2H), 7.36 (m, 4H), 7.28 (t, 2H), 7.08 (m, 2H), 3.99 (m, 2H), 3.70, (m, 2H), 3.66 (q, 2H), 2.10 (m, 2H), 1.99 (m, 2H), 1.08 (t, 3H). MS Atmospheric Pressure Chemical Ionization Mass Spectra: 338 (M$^+$+1).

(B) 4-Aminotetrahydropyran-4-Carboxylic Acid Ethyl Ester

To a solution of 4-[N-(diphenylmethylene)amino] tetrahydropyran-4-carboxylic acid ethyl ester (16.0 grams, 0.047 mole) in diethyl ether (120 mL) was added 1M aqueous hydrochloric acid solution (100 mL). The mixture was stirred vigorously at room temperature for 16 hours. The layers were separated and the aqueous layer washed with diethyl ether. The aqueous layer was brought to pH 10 with dilute aqueous ammonium hydroxide solution and extracted with dichloromethane. The organic extract was dried over sodium sulfate and concentrated to give 4-aminotetrahydropyran-4-carboxylic acid ethyl ester (7.128 g, 71.7%) as an oil.

$^1$HNMR (CDCl$_3$) δ 4.15 (q, 2H), 3.82 (m, 2H), 3.62 (m, 2H), 2.07 (m, 2H), 1.60 (s, 2H), 1.44 (m, 2H), 1.24 (t, 3H). $^{13}$CNMR (CDCl$_3$) d 176.48, 63.70, 61.09, 54.78, 35.05, 14.15. MS Atmospheric Pressure Chemical Ionization Mass Spectra: 210 (M$^+$+1).

(C) 4-[4-(4-Fluorophenoxy)Benzenesulfonylamino] Tetrahydropyran-4-Carboxylic Acid Ethyl Ester To a solution of 4-aminotetrahydropyran-4-carboxylic acid ethyl ester (7.00 grams, 0.0404 mole) in N,N-dimethylformamide (40 mL) was added triethylamine (5.94 mL, 0.043 mole). Solid 4-(4-fluorophenoxy)benzenesulfonyl chloride (12.165 grams, 0.0424 mole) was added in portions. The resulting mixture was stirred at room temperature for 16 hours and then most of the solvent was removed by evaporation under vacuum. The residue was partitioned between saturated sodium bicarbonate solution and dichloromethane. The aqueous layer was extracted with dichloromethane. The combined organic layers were washed with brine and dried over sodium sulfate. Evaporation of the solvent under vacuum provided crude 4-[4-(4-fluorophenoxy)benzenesulfonylamino]tetrahydropyran-4-carboxylic acid ethyl ester as an amber oil (21.05 grams). Flash chromatography on silica gel eluting with 25% ethyl acetate/hexane followed by 50% ethyl acetate/hexane provided 4-[4-(4-fluorophenoxy)benzenesulfonylamino] tetrahydropyran-4-carboxylic acid ethyl ester as an off-white crystalline solid (12.15 grams, 71%, mp 116–117° C.).

$^1$HNMR (CDCl$_3$) δ 7.79 (d, 2H), 7.09 (t, 2H) 7.02 (m, 2H), 6.97 (d, 2H), 5.10 (s, 1H), 4.01 (q, 2H), 3.60 (m, 4H), 2.08 (m, 2H), 1.84 (br d, 2H), 1.23 (t, 3H). M S Atmospheric Pressure Chemical Ionization Mass Spectra: 424 (M$^+$+1).

(D) 4-[4-(4-Fluorophenoxy)-Benzenesulfonylamino] Tetrahydropyran-4-Carboxylic Acid Method A A solution of 4-[4-(4-fluorophenoxy) benzenesulfonylamino]tetrahydropyran-4-carboxylic acid ethyl ester (12.1 grams, 0.0286 mole) in tetrahydrofuran (190 mL) was treated with aqueous 3 M sodium hydroxide solution (95 mL, 0.286 mole) and stirred at room temperature for 4 days. The solvent was evaporated under vacuum and the residue partitioned between water and diethyl ether. The aqueous layer was washed with diethyl ether, acidified to pH 1 with 3N aqueous hydrochloric acid solution and extracted with dichloromethane. After washing with water, the organic extract was dried over sodium sulfate, and concentrated to give 4-[4-(4-fluorophenoxy)-benzenesulfonylamino]tetrahydropyran-4-carboxylic acid (11.241 grams, 99%) as a yellowish solid foam.

Method B

A solution of 4-[4-(4-fluorophenoxy) benzenesulfonylamino]tetrahydropyran-4-carboxylic acid ethyl ester (34.19 grams, 0.807 mole) in ethanol (330 mL) was treated with aqueous 3 M sodium hydroxide solution (330 mL, 0.990 mole) and heated to reflux overnight. The solvent was evaporated under vacuum and the residue partitioned between water and diethyl ether. The aqueous layer was washed with diethyl ether, acidified to pH 1 with 3N aqueous hydrochloric acid solution and extracted with ethyl acetate. After washing with water, the organic extract was dried over sodium soulfate, and concentrated to give 4-[4-(4-fluorophenoxy)benzenesulfonylamino] tetrahydropyran-4-carboxylic acid (31.26 grams, 98%) as a white crystalline solid. $^1$HNMR (CDCl$_3$) δ 7.73 (d, 2H), 7.03 (t, 2H) 6.96 (m, 2H), 6.91 (d, 2H), 3.56 (m, 2H), 3.43 (br m, 3H), 2.01 (m, 2H), 1.80 (br d, 2H). MS Atmospheric Pressure Chemical Ionization Mass Spectra: 394 (M$^+$−1) (-ion).

(E) 4-[4-(4-Fluorophenoxy)Benzenesulfonylamino] Tetrahydropyran-4-Carboxylic Acid N-Benzyloxyamide Diisopropyl ethylamine (3.89 grams, 0.030 mole) and (benzotriazol-1-yloxy)tris-(dimethylamino)-phosphonium hexafluorophosphate (13.27 grams, 0.030 mole) were added sequentially to a solution of 4-[4-(4-fluorophenoxy)-benzenesulfonylamino] tetrahydropyran-4-carboxylic acid (11.22 grams, 0.028 mole) in anhydrous N,N-dimethylformamide (140 mL). The resulting solution was stirred at room temperature for 16 hours. Additional diisopropyl ethylamine (4.0 mL, 0.051 mole) and O-benzyl hydroxylamine hydrochloride (5.46 grams, 0.034 mole) were then added and the resulting mixture was stirred at 60° C. for 18 hours. After concentration under vacuum, the residue was treated with 0.5N aqueous hydrochloric acid solution and extracted with ethyl acetate. The organic extract was washed with saturated aqueous sodium bicarbonate solution, water, and brine. The solution was dried over magnesium sulfate, filtered and concentrated to one fourth original volume. Addition of an equal volume of hexane precipitated 4-[4-(4-fluorophenoxy) benzenesulfonylamino]-tetrahydropyran-4-carboxylic acid N-benzyloxyamide (11.595 g, 81.6%) as a white crystalline solid (mp 175–176° C.).

$^1$HNMR (CDCl$_3$) δ 7.76 (d, 2H), 7.35 (m, 5H), 7.05 (t, 2H), 6.96 (m, 4H) 5.38 (br s, 1H), 4.86 (s, 2H), 3.57 (m, 2H), 3.44 (m, 2H), 2.01 (m, 2H), 1.77 (br d, 2H), 1.54 (br s, 1H). MS Atmospheric Pressure Chemical Ionization 501 (M$^+$+1).

(F) 4-[4-(4-Fluorophenoxy)Benzenesulfonylamino]-Tetrahydropyran-4-Carboxylic Acid Hydroxyamide Method A A solution of 4-[4-(4-fluorophenoxy) benzenesulfonylamino]tetrahydropyran-4-carboxylic acid N-benzyloxyamide(11.28 grams, 0.0225 mole) in ethyl acetate (600 mL) was treated with 5% palladium on barium sulfate (5.0 grams) and hydrogenated in a Parr™ shaker at 3 atmospheres pressure for 18 hours. After filtration through nylon (pore size 0.45 mm) to remove the catalyst, the filter pad was rinsed with methanol. Combined filtrate and rinse were evaporated and the residue taken up in hot methanol. Cooling afforded crude 4-[4-(4-fluorophenoxy) benzenesulfonylamino]-tetrahydropyran-4-carboxylic acid hydroxyamide (5.941 grams, 64%, mp 176–177° C.) as a white crystalline solid. The mother liquor was evaporated and the residue crystallized from 50% methanoldichloromethane to give additional 4-[4-(4-fluorophenoxy) benzenesulfonylamino]-tetrahydropyran-4-carboxylic acid hydroxyamide (0.660 grams, mp 184–185° C.) as white needles. The mother liquor was again evaporated and the residue crystallized from methanol/dichloromethane to give additional product (1.861 grams, mp 176–177° C.). Recrystallization of the first lot from methanol/dichloromethane provided analytically pure 4-[4-(4-fluorophenoxy) benzenesulfonylamino]tetrahydropyran-4-carboxylic acid hydroxyamide (3.091 grams, mp 184–185° C.).

Method B

Oxalyl chloride (11.83 grams, 0.0932 mole, 1.1 eq.) and DMF (0.13 mL) were added to a stirred suspension of the carboxylic acid (33.25 grams, 0.0841 mole) in dry methylene chloride (300 mL) at room temperature. Some bubbling was observed. The suspension, 30 which slowly became a yellowish solution was stirred overnight at room temperature. Meanwhile, a solution of hydroxylamine hydrochloride (7.65 grams, 0.110 mole, 1.3 eq.) in dry pyridine (51.4 mL, 0.635 mole, 7.5 eq.) at 0° C. was treated with chlorotrimethylsilane causing a white precipitate to form. This suspension was stirred at room temperature overnight. Both flasks were then cooled to 0° C. and the solution of acid chloride was added to the suspension of silylated hydroxylamine. The resulting mixture was stirred at 0° C. for 1 hour and room temperature for 2 hours. Added 1000 mL aqueous 2N HCl and stirred at room temperature for 1 hour. The layers were separated, the aqueous layer was extracted, three times with ethylacetate (500 mL). Combined organic layers were washed with water and brine and dried over magnesium sulfate, filtered and the volume of the filtrate reduced to 300 mL at which point a large amount of white crystalline solid had precipitated. This was cooled overnight in a refrigerator. The solid was collected by vacuum filtration, rinsed with cold 1:1 ethylacetate/hexane and dried under high vacuum to give 30.311 grams of the desired hydroxamic acid (87.8%) as a white crystalline solid (mp 189–190° C.).

$^1$HNMR (d$_6$ DMSO) δ 10.35 (br s, 1H), 8.68 (br s, 1H), 7.78 (br s, 1H), 7.74 (d, 2H), 7.26 (t, 2H), 7.16 (m, 2H), 7.04 (d, 2H), 3.40 (m, 2H), 3.31 (m, 2H), 1.78 (m, 4H). $^{13}$CNMR (DMSO) δ 169.65, 160.66, 137.50, 129.39, 122.34, 122.25, 117.75, 117.44, 117.24, 62.94, 58.45, 33.34. MS Atmospheric Pressure Chemical Ionization Mass Spectra: 409 (M$^+$–1) (-ion).

PREPARATION A 4-(4-Fluorophenoxy)Benzenesulfonyl Chloride

Chlorosulfonic acid (26 mL, 0.392 mole) was added dropwise to ice-cooled 4-fluorophenoxybenzene (36.9 grams, 0.196 mole) with mechanical stirring. When addition was complete, the mixture was stirred at room temperature for 4 hours. The mixture was then poured into ice water. The product. 4-4-fluorophenoxy)benzene-sulfonylchloride (18.6 grams, 33%) was collected by filtration and dried in the air.

PREPARATION B

Sodium 4-(3-Methylbutoxy)Benzenesulfonate

A solution of 4-hydroxybenzenesulfonic acid (10.0 grams, 43.1 mmole) and sodium hydroxide (3.3 grams, 83 mmole) in water (40 mL) was mixed with a solution of 1-iodo-3-methylbutane (11.3 mL, 86.4 mmole) in isopropanol (60 mL) and the resulting mixture was heated at reflux for 2 days. The isopropanol was removed by evaporation under vacuum. The title compound, 10.0 grams (87%), was collected by filtration and washed with isopropanol.

PREPARATION C 4-(3-Methylbutoxy)Benzenesulfonyl Chloride

A mixture of sodium 4-(3-methylbutoxy) benzenesulfonate (2.5 grams, 9.4 mmole), thionyl chloride (10 mL), and 5 drops of N,N-dimethylformamide was heated at reflux for 5 hours. After cooling, the excess thionyl chloride was evaporated and the residue was taken up in ethyl acetate. The solution was cooled in an ice bath and water was added. The organic phase was separated and washed with water and brine. After drying over sodium sulfate, the solvent was evaporated to afford the title compound as an oil, 2.34 grams (95%).

PREPARATION D

Sodium 4-(2-Cyclopentylethoxy)Benzenesulfonate

A solution of 4-hydroxybenzenesulfonic acid (6.5 grams, 28.2 mmole) and sodium hydroxide (2.2 grams, 55 mmole) in water (15 mL) was mixed with a solution of 2-(bromoethyl)cyclopentane (15.0 grams, 84.7 mmole) in isopropanol (40 mL) and the resulting mixture was heated at reflux for 2 days. The isopropanol was removed by evaporation under vacuum. The titled compound, 4.7 grams (57%), was collected by filtration and washed with isopropanol.

PREPARATION E 4-(3-Methylbutoxy)Benzenesulfonyl Chloride

A mixture of sodium 4-(2-cyclopentylethoxy) benzenesulfonate (2.5 grams, 8.6 mmole), thionyl chloride (15 mL), and a few drops of N,N-dimethylformamide was heated at reflux for 5 hours. After cooling, the excess thionyl chloride was evaporated and the residue was taken up in ethyl acetate. The solution was cooled in an ice bath and water was added. The organic phase was separated and washed with water and brine. After drying over sodium sulfate, the solvent was evaporated to afford the title compound as an oil, 2.24 grams (90%).

PREPARATION F

4-Fluorobiphenylsulfonyl Chloride

Chlorosulfonic acid (8.7 mL, 0.13 mole) was added dropwise to 4-fluorobiphenyl (10.2 grams, 59 mmol) while stirring in an ice bath. Stirring was continued with ice cooling for 0.5 hours and then the reaction mixture was poured onto ice. The resulting white precipitate was collected by filtration and dissolved in chloroform. The chloroform solution was washed with water and brine, dried over magnesium sulfate and concentrated to afford a white solid. The desired product, 4-fluorobiphenylsulfonyl chloride (4.3 grams, 27%), was separated from 4-fluorobiphenylsulfonic acid (an unwanted side product) by crystallization of the latter from ethyl acetate and crystallization of the remaining material from hexane.

PREPARATION G

Sodium 4-(4-Fluorobenzyloxy)Benzenesulfonate

To a solution of 4-hydroxybenzenesulfonic acid (5.13 grams, 22.1 mmole) in 1N aqueous sodium hydroxide solution (23 mL) was added a solution of 4-fluorobenzylbromide (3.3 mL, 26.5 mmole) in ethanol (20 mL). The resulting mixture was heated at reflux for 2 days. Upon cooling and standing, a white solid precipitated. The precipitated product, sodium 4-(4-fluorobenzyloxy) benzenesulfonate, 4.95 grams (74%) was collected by filtration and washed with ethyl acetate and diethyl ether.

PREPARATION H 4-(4-Fluorobenzyloxy)Benzenesulfonyl Chloride

To a slurry of sodium 4-(4-fluorobenzyloxy) benzenesulfonate (0.5 grams, 1.64 mmole), in methylene chloride (5 mL) was added phosphorus pentachloride (275 mg, 1.31 mmole). The resulting mixture was heated at reflux for 7 hours. After cooling in an ice bath and quenching with water (15 mL), the mixture was extracted with ethyl acetate. The organic phase was washed with brine, dried over sodium sulfate, and concentrated to afford 4-(4-fluorobenzyloxy)benzenesulfonyl chloride a white solid (130 mg, 26%).

PREPARATION I 4-(4-Chlorophenoxy)Benzenesulfonyl Chloride

Chlorosulfonic acid (9.7 mL, 0.147 mole) was added dropwise to 4-chlorophenoxybenzene (12.6 mL, 73.4 mmole) at room temperature with stirring. When addition was complete, the mixture was stirred at room temperature for 1 hour and then poured into ice water. The solid was collected by filtration, dried in the air, and recrystallized from petroleum ether and ethyl acetate to give 4-(4-chlorophenoxy)benzenesulfonylchloride (7.43 grams, 33%).

What is claimed is:

1. A compound of the formula

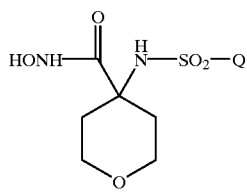

I or the pharmaceutically acceptable salts thereof, wherein

Q is $(C_1-C_6)$alkyl, $(C_6-C_{10})$aryl, $(C_2-C_9)$heteroaryl, $(C_6-C_{10})$aryloxy$(C_1-C_6)$alkyl, $(C_6-C_{10})$aryloxy $(C_6-C_{10})$aryl, $(C_6-C_{10})$aryloxy$(C_2-C_9)$heteroaryl, $(C_6-C_{10})$aryl$(C_1-C_6)$alkyl, $(C_6-C_{10})$aryl$(C_6-C_{10})$aryl, $(C_6-C_{10})$aryl$(C_2-C_9)$heteroaryl, $(C_6-C_{10})$aryl$(C_6-C_{10})$ aryl$(C_1-C_6)$alkyl, $(C_6-C_{10})$aryl$(C_6-C_{10})$aryl$(C_6-C_{10})$ aryl, $(C_6-C_{10})$aryl$(C_6-C_{10})$aryl$(C_2-C_9)$heteroaryl, $(C_2-C_9)$heteroaryl$(C_1-C_6)$alkyl, $(C_2-C_9)$heteroaryl $(C_6-C_{10})$aryl, $(C_2-C_9)$heteroaryl$(C_2-C_9)$heteroaryl, $(C_6-C_{10})$aryl$(C_1-C_6)$alkoxy$(C_1-C_6)$alkyl, $(C_6-C_{10})$ aryl$(C_1-C_6)$alkoxy$(C_6-C_{10})$aryl, $(C_6-C_{10})$aryl$(C_1-C_6)$ alkoxy$(C_2-C_9)$heteroaryl, $(C_2-C_9)$heteroaryloxy $(C_1-C_6)$alkyl, $(C_2-C_9)$heteroaryloxy$(C_6-C_{10})$aryl, $(C_2-C_9)$heteroaryloxy$(C_2-C_9)$heteroaryl, $(C_2-C_9)$ heteroaryl$(C_1-C_6)$alkoxy$(C_1-C_6)$alkyl, $(C_2-C_9)$ heteroaryl$(C_1-C_6)$alkoxy$(C_6-C_{10})$aryl or $(C_2-C_9)$ heteroaryl$(C_1-C_6)$alkoxy$(C_2-C_9)$heteroaryl;

wherein each $(C_6-C_{10})$aryl or $(C_2-C_9)$heteroaryl moieties of said $(C_6-C_{10})$aryl, $(C_2-C_9)$heteroaryl, $(C_6-C_{10})$ aryloxy$(C_1-C_6)$alkyl, $(C_6-C_{10})$aryloxy$(C_6-C_{10})$aryl, $(C_6-C_{10})$aryloxy$(C_2-C_9)$heteroaryl, $(C_6-C_{10})$aryl $(C_1-C_6)$alkyl, $(C_6-C_{10})$aryl$(C_6-C_{10})$aryl, $(C_6-C_{10})$aryl $(C_2-C_9)$heteroaryl, $(C_6-C_{10})$aryl$(C_6-C_{10})$aryl$(C_1-C_6)$ alkyl, $(C_6-C_{10})$aryl$(C_6-C_{10})$aryl$(C_6-C_{10})$aryl, $(C_6-C_{10})$aryl$(C_6-C_{10})$aryl$(C_2-C_9)$heteroaryl, $(C_2-C_9)$ heteroaryl$(C_1-C_6)$alkyl, $(C_2-C_9)$heteroaryl$(C_6-C_{10})$ aryl, $(C_2-C_9)$heteroaryl$(C_2-C_9)$heteroaryl, $(C_6-C_{10})$ aryl$(C_1-C_6)$alkoxy$(C_1-C_6)$alkyl, $(C_6-C_{10})$aryl$(C_1-C_6)$ alkoxy$(C_6-C_{10})$aryl, $(C_6-C_{10})$aryl$(C_1-C_6)$alkoxy $(C_2-C_9)$heteroaryl, $(C_2-C_9)$heteroaryloxy$(C_1-C_6)$ alkyl, $(C_2-C_9)$heteroaryloxy$(C_6-C_{10})$aryl, $(C_2-C_9)$ heteroaryloxy$(C_2-C_9)$heteroaryl, $(C_2-C_9)$heteroaryl $(C_1-C_6)$alkoxy$(C_1-C_6)$alkyl, $(C_2-C_9)$heteroaryl $(C_1-C_6)$alkoxy$(C_6-C_{10})$aryl or $(C_2-C_9)$heteroaryl $(C_1-C_6)$alkoxy$(C_2-C_9)$heteroaryl is optionally substituted on any of the ring carbon atoms capable of forming an additional bond by one or more substituents per ring independently selected from fluoro, chloro, bromo, $(C_1-C_6)$alkyl, $(C_1-C_6)$alkoxy, perfluoro $(C_1-C_3)$alkyl, perfluoro$(C_1-C_3)$alkoxy and $(C_6-C_{10})$ aryloxy;

or a pharmaceutically acceptable salt thereof.

2. A compound according to claim 1, wherein Q is optionally substituted $(C_6-C_{10})$aryl, $(C_6-C_{10})$aryl$(C_6-C_{10})$ aryl, $(C_6-C_{10})$aryloxy$(C_6-C_{10})$aryl, $(C_6-C_{10})$aryloxy $(C_2-C_9)$heteroaryl, $(C_2-C_9)$heteroaryl, $(C_2-C_9)$heteroaryl $(C_2-C_9)$heteroaryl, $(C_6-C_{10})$aryl$(C_2-C_9)$heteroaryl, $(C_2-C_9)$heteroaryl$(C_6-C_{10})$aryl, $(C_2-C_9)$heteroaryloxy $(C_6-C_{10})$aryl, $(C_6-C_{10})$aryl$(C_1-C_6)$alkoxy$(C_6-C_{10})$-aryl, or $(C_2-C_9)$heteroaryl$(C_1-C_6)$alkoxy$(C_6-C_{10})$aryl.

3. A compound according to claim 1, wherein Q is optionally substituted $(C_6-C_{10})$aryloxy$(C_6-C_{10})$aryl.

4. A compound according to claim 3, wherein the $(C_6-C_{10})$aryloxy ring of said $(C_6-C_{10})$aryloxy$(C_6-C_{10})$aryl group is optionally mono-substituted in the 4-position of the ring.

5. A compound according to claim 1, wherein said compound is selected from the group consisting of:

4-[4-(4-fluorophenoxy)benzenesulfonylamino] tetrahydropyran-4-carboxylic acid hydroxyamide;

4-[4-(4-chlorophenoxy)benzenesulfonylamino] tetrahydropyran-4-carboxylic acid hydroxyamide;

4-[4-(phenoxy)benzenesulfonylamino]tetrahydropyran-4-carboxylic acid hydroxyamide;

4-[4-(4-pyridyloxy)benzenesulfonylamino] tetrahydropyran-4-carboxylic acid hydroxyamide;

4-[4-(4-fluorophenyl)benzenesulfonylamino] tetrahydropyran-4-carboxylic acid hydroxyamide;

4-[4-(4-fluorophenylmethoxy)bezenesulfonylamino] tetrahydropyran-4-carboxylic acid hydroxyamide;

(phenylmethoxy)benzenesulfonylamino]tetrahydropyran-4-carboxylic acid hydroxyamide; and 4-[4-(4-Fluorophenylethoxy)benzenesulfonylamino]tetrahydropyran-4-carboxylic acid hydroxyamide.

6. A pharmaceutical composition for the treatment of a condition selected from the group consisting of arthritis (including osteoarthritis and rheumatoid arthritis), inflammatory bowel disease, Crohn's disease, emphysema, chronic obstructive pulmonary disease, Alzheimer's disease, organ transplant toxicity, cachexia, allergic reactions, allergic contact hypersensitivity, cancer, tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neuro-degenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis and septic shock in a mammal, including a human, comprising an amount of a compound of claim 1 effective in such treatment and a pharmaceutically acceptable carrier.

7. A method for treating a condition selected from the group consisting of arthritis (including osteoarthritis and rheumatoid arthritis), inflammatory bowel disease, Crohn's disease, emphysema, chronic obstructive pulmonary disease, Alzheimer's disease, organ transplant toxicity, cachexia, allergic reactions, allergic contact hypersensitivity, cancer, tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neuro-degenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis and septic shock in a mammal, including a human, comprising administering to said mammal an amount of a compound of claim 1, effective in treating such a condition.

8. A pharmaceutical composition for the treatment of a condition which can be treated by the inhibition of matrix metalloproteinases in a mammal, including a human, comprising an amount of a compound of claim 1 effective in such treatment and a pharmaceutically acceptable carrier.

9. A pharmaceutical composition for the treatment of a condition which can be treated by the inhibition of a mammalian reprolysin in a mammal, including a human, comprising an amount of a compound of claim 1 effective in such treatment and a pharmaceutically acceptable carrier.

10. A method for the inhibition of matrix metalloproteinases in a mammal, including a human, comprising administering to said mammal an effective amount of a compound of claim 1.

11. A method for the inhibition of a mammalian reprolysin in a mammal, including a human, comprising administering to said mammal an effective amount of a compound of claim 1.

* * * * *